United States Patent
Higo (10) Patent No.: US 6,650,127 B2
(45) Date of Patent: Nov. 18, 2003

(54) APPARATUS FOR MEASURING CONDUCTIVITY

(75) Inventor: Yuji Higo, Tokyo (JP)

(73) Assignee: Organo Corporation, Tokyo (JP)

( * ) Notice: Subject to any disclaimer, the term of this patent is extended or adjusted under 35 U.S.C. 154(b) by 54 days.

(21) Appl. No.: 10/009,312

(22) PCT Filed: Feb. 13, 2001

(86) PCT No.: PCT/JP01/00982
§ 371 (c)(1),
(2), (4) Date: Oct. 22, 2001

(87) PCT Pub. No.: WO01/63269
PCT Pub. Date: Aug. 30, 2001

(65) Prior Publication Data
US 2003/0155937 A1 Aug. 21, 2003

(30) Foreign Application Priority Data
Feb. 22, 2000 (JP) ............................... 2000-44495

(51) Int. Cl.[7] ............................................. G01R 27/26
(52) U.S. Cl. ...................... 324/702; 324/691; 324/444
(58) Field of Search .................. 324/441, 687, 324/444, 447, 691, 693, 696, 702

(56) References Cited

U.S. PATENT DOCUMENTS

| | | | | |
|---|---|---|---|---|
| 4,853,638 A | * | 8/1989 | Endou et al. | 324/441 |
| 5,223,796 A | * | 6/1993 | Waldman et al. | 324/687 |
| 5,847,423 A | * | 12/1998 | Yamamichi | 257/296 |
| 6,264,825 B1 | * | 7/2001 | Blackburn et al. | 205/777.5 |

FOREIGN PATENT DOCUMENTS

| | | |
|---|---|---|
| JP | 6-34700 | 9/1994 |
| JP | 8-278270 | 10/1996 |
| JP | 9-89827 | 4/1997 |
| JP | 11-198633 | 7/1999 |

* cited by examiner

Primary Examiner—Jay Patidar
Assistant Examiner—Vincent Q. Nguyen
(74) Attorney, Agent, or Firm—Norris McLaughlin & Marcus (57) ABSTRACT

An apparatus for measuring electric conductivity having three electrodes brought into contact with a substance to be measured. The electrodes include a detection electrode for detecting electric conductivity of the substance to be measured, and two AC current supply electrodes disposed on both sides of the detection electrode at respective distances, and an AC current of the same phase is applied to the two AC current supply electrodes. This apparatus provides stabilized measurement of the electric conductivity of a substance to be measured with a high accuracy.

6 Claims, 5 Drawing Sheets

PRIOR ART

APPARATUS FOR MEASURING CONDUCTIVITY

This application is a 371 of PCT/JP01/00982, filed on Feb. 13, 2001.

TECHNICAL FIELD OF THE INVENTION

The present invention relates to an apparatus for measuring electric conductivity, and specifically, relates to an apparatus for measuring electric conductivity capable of measuring electric conductivity of a substance to be measured stably and accurately at all times.

BACKGROUND OF THE INVENTION

Electric conductivity is especially employed as a scale to measure a concentration of ions capable of migrating in an aqueous solution, and an apparatus for measuring electric conductivity is used to measure ion concentrations in many kinds of aqueous solutions. An apparatus for measuring electric conductivity, generally, determines an increase or a decrease of the ion concentration of an aqueous solution by measuring the resistance of the aqueous solution existing between an electric conductivity detection electrode and an electric current supply electrode connected to a power source.

Figure 9:
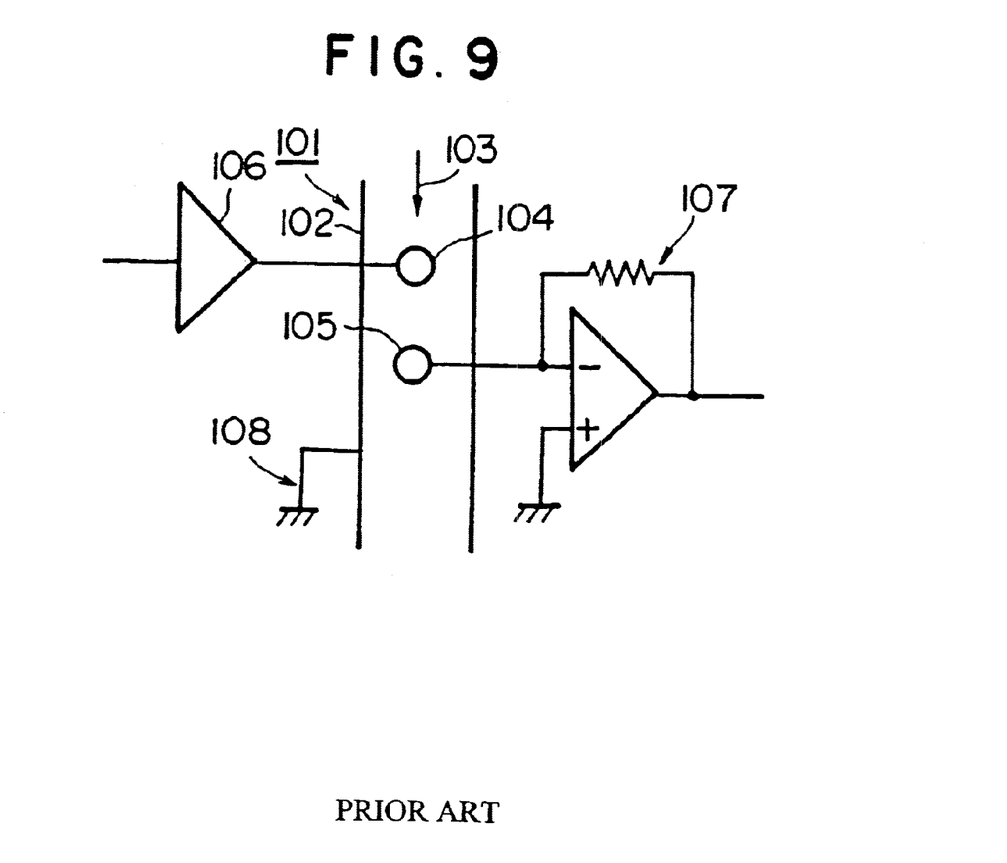
FIG. 9 is a schematic block diagram of a conventional apparatus for measuring electric conductivity.

Namely, a conventional apparatus for measuring electric conductivity is constituted, for example, as depicted in FIG. 9. In an apparatus for measuring electric conductivity 101 shown in FIG. 9, a power source electrode 104 and a detection electrode 105 for detecting electric conductivity are disposed apart from each other relative to a fluid 103 to be measured which flows into a measurement tube 102 or which is stored in the measurement tube 102. An AC constant voltage is applied to the power source supply electrode 104, for example, from a power source (not shown) through an amplifier 106. An electric current from the detection electrode 105 for detecting electric conductivity is output through an electric current amplifier 107, and is served for measuring electric conductivity. The measurement tube 102 is composed of an insulation material (for example, a polyvinyl chloride tube) at at least above-described portion for measuring electric conductivity, but the measurement tube is usually in a substantially grounded condition (a grounded point 108) at any position of extending portion of the tube.

In the apparatus for measuring electric conductivity 101 thus constructed, since a resistance corresponding to an electric conductivity of the fluid 103 to be measured exists between the electrodes 104 and 105, a small electric current flowing from the power source electrode 104 to the electric conductivity detection electrode 105 via the resistance is amplified by the electric current amplifier 107, and an output signal therefrom is determined as a value corresponding to the electric conductivity of the fluid to be measured.

However, in the apparatus for measuring electric conductivity 101 having such a constitution, since the measurement tube 102 is substantially grounded at any position of the extending portion thereof, an electric current from the electric conductivity detection electrode 105 flows into the electric current amplifier 107, and at the same time, a smaller electric current flows into the grounded point 108. Namely, from the electric conductivity detection electrode 105, a current leakage occurs more or less, independently of the electric current for measuring electric conductivity.

Since the position of the grounded point 108 is not fixed, and therefore the resistance between the electrode 105 and the grounded point 108 varies, and since a small electric current flowing between them flows into the electric current amplifier 107 via the earth, the leaked electric current flowing from the-above-described electrode 105 to the grounded point 108 is a factor varying the electric current detected from the electric conductivity detection electrode 105. Therefore, the existence of such a leaked electric current causes the measurement accuracy of the electric conductivity to be reduced. Further, the variation of the leaked electric current induces not only reduction of the measurement accuracy of the electric conductivity but also scattering of measured data of the electric conductivity.

DISCLOSURE OF THE INVENTION

Accordingly, it is an object of the present invention to provide an apparatus for measuring electric conductivity capable of measuring electric conductivity with a high accuracy by measuring electric conductivity of a substance to be measured stably at a condition with no variability at all times.

Further, it is another object to measure electric conductivity stably and accurately especially through the entire measuring period even when organic substances are contained in a substance to be measured, while making the above-described high-accuracy measurement possible.

To accomplish the above-described objects, the present invention relates to an apparatus for measuring electric conductivity comprising three electrodes brought into contact with a substance to be measured, the three electrodes including a detection electrode for detecting electric conductivity of the substance to be measured, and two AC current supply electrodes disposed on both sides of the electric conductivity detection electrode with respective distances, an AC current of the same phase being applied to the two AC current supply electrodes (a first apparatus for measuring electric conductivity). A substance to be measured is generally an aqueous solution, but a gaseous or slurry-like substance can also be measured.

In this first apparatus for measuring electric conductivity, although it is preferred that a constant voltage with the same electric potential is applied to the above-described two AC current supply electrodes, the potentials of the voltages applied to the two AC current supply electrodes may be different from each other. However, even in the latter case, the voltages applied to the respective AC current supply electrodes are to be predetermined constant voltages.

Further, an apparatus for measuring electric conductivity according to the present invention comprises three electrodes brought into contact with a substance to be measured, the three electrodes including a detection electrode for detecting electric conductivity of the substance to be measured, an AC current supply electrode disposed on one side of the electric conductivity detection electrode with a distance, and a grounded electrode disposed on the other side of the electric conductivity detection electrode with a distance (a second apparatus for measuring electric conductivity).

In this second apparatus for measuring electric conductivity, it is preferred that a constant voltage is applied to the above-described AC current supply electrode.

In the first and second apparatuses for measuring electric conductivity as described above, when organic substances and the like are contained in a substance to be measured, advantage can be taken of the photocatalytic activity of titanium oxide which decomposes organic substances or the super-hydrophilicity of titanium oxide in order to efface the influence on the measurement of electric conductivity exerted by adhesion or adsorption of organic substances to the electrode surfaces.

Namely, each of the above-described three electrodes can be constructed so that its electrode surface is formed by a titanium oxide layer provided on a surface of an electrode body made of a conductive metal. It is preferred that light irradiating means is disposed against the titanium oxide layer to exhibit a photocatalytic activity on the titanium oxide layer. For example, a construction can be employed, wherein the apparatus has a space for storing a substance to be measured defined between respective electrode surfaces of the above-described three electrodes, and light irradiating means that irradiates light onto the respective electrode surfaces.

In these apparatuses for measuring electric conductivity, it is preferred that the light irradiated by the above-described light irradiating means has a wavelength which brings about a photocatalytic activity of the titanium oxide layer. For example, light with a wavelength from about 300 to about 400 nm can be employed. As means for irradiating light, a light source composed of means for irradiating ultraviolet rays and the like such as a black light may be directly employed, and a light guiding material (for example, an optical fiber, or tube and the like comprising a light guiding raw material) to guide light from a light source provided as means for irradiating light may also be employed. Further, the light from a light guiding material may be added to light irradiated directly from a light source.

Further, the above-described space for storing a substance to be measured may be defined by a light transmitting material, and it may be constituted so that the light from the light irradiating means is irradiated onto an electrode surface through the light transmitting material (for example, glass). In this case, if a titanium oxide coating layer capable of transmitting light is provided on the surface of the light transmitting material at its side facing the space for storing a substance to be measured (a surface in contact with solution), adhesion of organic substances and the like to this surface of the light transmitting material can be prevented by super-hydrophilicity and organics decomposition property ascribed to the titanium oxide layer.

Further, the above-described electrode can be produced by, for example, the following method. Namely, a method can be employed wherein an electrode surface consists of a titanium oxide layer formed by a surface treatment such as sputtering, plating or the like on a surface of an electrode body made of a conductive metal. Alternatively, a method can also be employed wherein an electrode surface made of a titanium oxide layer is formed by providing oxygen to a surface of an electrode body made of titanium. As the method for forming a titanium oxide layer by providing oxygen, a method based on air oxidation other than a method utilizing electrolysis can be employed.

In the first apparatus for measuring electric conductivity according to the present invention as described above, the electric conductivity detection electrode is disposed between two AC current supply electrodes, and an AC current of the same phase is applied to the two AC current supply electrodes. By this constitution, the electric conductivity detection electrode is electrically shielded by the two AC current supply electrodes against any grounded portion existing outside of the positions where these three electrodes are disposed. Therefore, no resistance exists between the electric conductivity detection electrode and an outside grounded portion, and substantially any leaked electric current does not flow therebetween. As a result, an electric current for measuring electric conductivity can be obtained stably at all times from the electric conductivity detection electrode, and any scattering of the measured data of the electric conductivity can be prevented, and a high-accuracy measurement of the electric conductivity becomes possible.

Further, in the second apparatus for measuring electric conductivity according to the present invention, since an AC current is applied to only one electrode of the two electrodes disposed on both sides of the electric conductivity detection electrode and the other electrode is grounded, the portion between these two electrodes is set in a formation of so-called resistive division which is created by the electric conductivity detection electrode disposed therebetween. And, since a constant voltage is applied to the above-described one electrode, and the potential of the other grounded electrode is always zero, the resistance between the electric conductivity detection electrode and the grounded electrode can be fixed at a constant value substantially having no variation. Therefore, even if the measurement tube for the electric conductivity is in a grounded condition at any position of its extending portion, because the above-described other electrode is forcibly grounded before reaching the grounded point of the measurement tube, and the electric potential is focibly reduced to zero at the position of the electrode, there is no room to allow a resistance of high variability to enter between the electric conductivity detection electrode and the grounded point of the measurement tube. Consequently, an electric current for measuring electric conductivity can be obtained from the electric conductivity detection electrode stably at all times, and any scattering of the measured data of the electric conductivity can be prevented, and a high-accuracy measurement of the electric conductivity becomes possible.

Thus, in the apparatus for measuring electric conductivity according to the present invention, since the AC current supply electrodes are disposed, or the AC current supply electrode and the grounded electrode are disposed on the both sides of the detection electrode for detecting electric conductivity, and the electric conductivity detection electrode between both electrodes can be electrically shielded adequately against an outside grounded portion, any disturbance can be prevented from being generated in an electric current extracted from the electric conductivity detection electrode, and therefore, the electric conductivity of a substance to be measured can be measured with a high accuracy under the measurement condition being always stabilized.

Further, in such first and second apparatuses for measuring electric conductivity, if the electrodes having titanium oxide layers on their surfaces are used, the photocatalytic activity of titanium oxide is exhibited by irradiating light with an appropriate wavelength (for example, an ultraviolet ray) to the titanium oxide layers, organic substances in contact with the titanium oxide layers or existing in the water near the layers are decomposed, and the adhesion or adsorption thereof to the titanium oxide layers is prevented. Further, since at first water films are formed on the electrode surfaces by the super-hydrophilicity that the titanium oxide layers have, even if the decomposition of the organic substances is delayed, the adhesion itself can be suppressed. Therefore, the electrode surfaces are always maintained at a desirable surface condition without adhesion or adsorption of the organic substances, and the desirable surface condition is maintained stably at all times without requiring any periodical cleaning and the like. Therefore, without requiring a periodical cleaning of the electrode surfaces, electric conductivity can be measured stably and accurately at all times, and repeatability of the accuracy of the measurement can be ensured with no problems.

THE BEST MODE FOR CARRYING OUT THE INVENTION

Hereinafter, desirable embodiments of the present invention will be explained referring to Figures.

Figure 1:
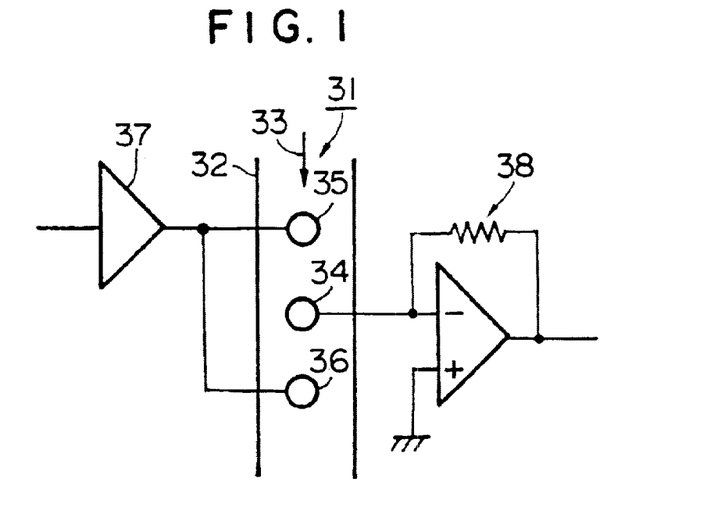
FIG. 1 is a schematic block diagram of an apparatus for measuring electric conductivity according to a first embodiment of the present invention.

FIG. 1 shows an apparatus for measuring electric conductivity according to a first embodiment of the present invention. In this apparatus 31 for measuring electric conductivity, three electrodes 34, 35, 36 are brought into contact with a fluid 33 to be measured which is sent into an insulated measurement tube 32, or which is stored in the measurement tube 32. The three electrodes comprise a detection electrode 34 for detecting electric conductivity, and two AC current supply electrodes 35, 36 disposed on both sides of the electric conductivity detection electrode 34 at respective distances. An AC current of the same phase with a constant voltage of the same potential is applied to the two AC current supply electrodes 35, 36 through an amplifier 37. The electric conductivity detection electrode 34 is connected to an electric current amplifier 38, and an amplified electric current is output as a value corresponding to an electric conductivity of the fluid 33 to be measured through the electric current amplifier 38.

Figure 2:
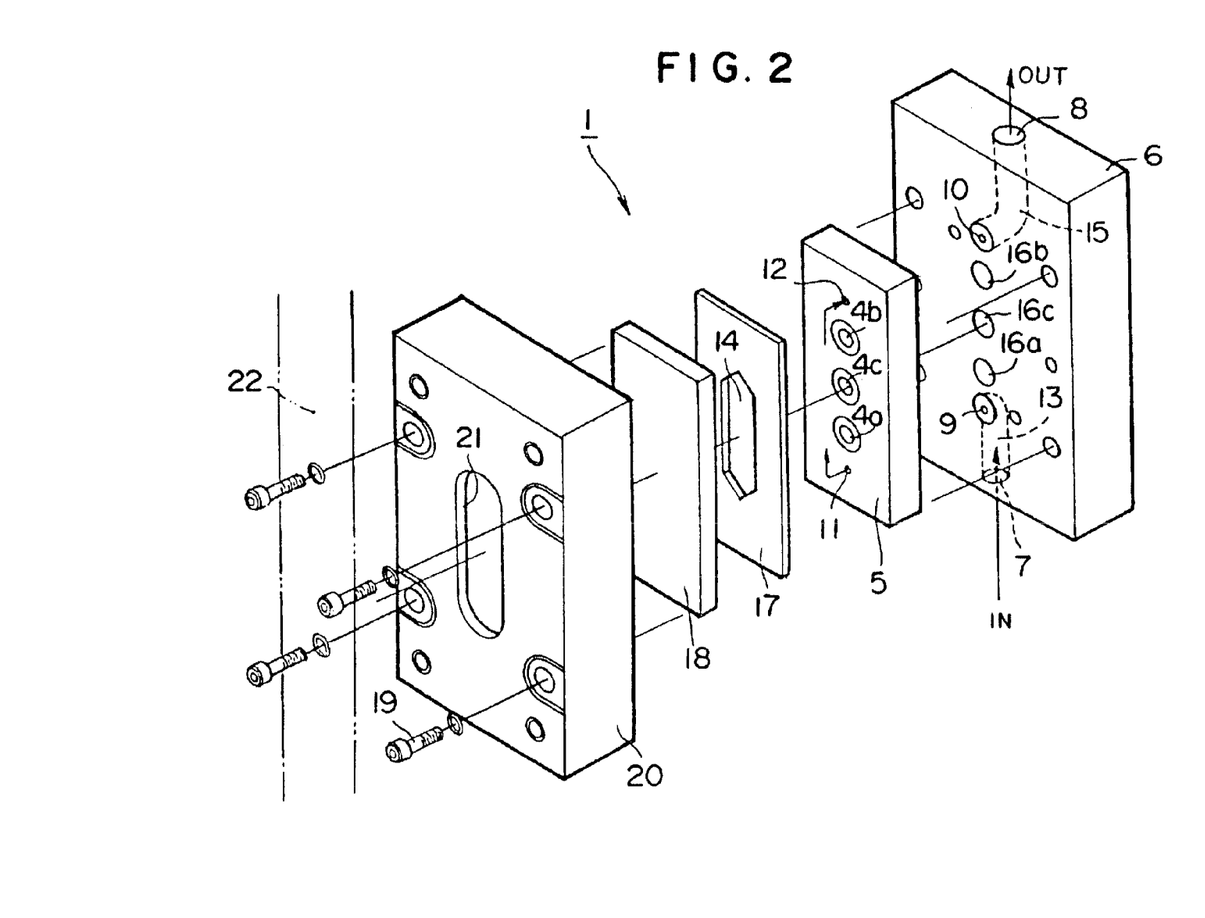
FIG. 2 is an exploded perspective view of an example wherein a portion for measuring electric conductivity of an apparatus for measuring electric conductivity according to the present invention is constructed as an electric conductivity meter.
Figure 3:
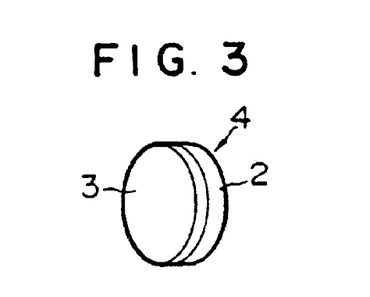
FIG. 3 is an enlarged perspective view of an electric conductivity measuring electrode of the electric conductivity meter depicted in FIG. 2.

A portion for measuring electric conductivity in the apparatus 31 can be constituted as an electric conductivity meter 1, for example, as shown in FIG. 2. In this electric conductivity meter 1, an electric conductivity measuring electrode 4, wherein the electrode surface is formed by a titanium oxide layer 3 provided on a surface of an electrode body 2 made of a conductive metal, as shown in FIG. 3, is used. The titanium oxide layer 3 is formed by a surface treatment (such as sputtering, plating and the like) of an electrode body made of a conductive metal, or is formed by oxidizing the surface of the electrode body 2 made of titanium. The oxidation is conducted by electrolysis or air oxidation.

The electric conductivity measuring electrodes 4 are used as electrodes corresponding to three electrodes 34, 35, 36 shown in FIG. 1, and are attached to an electrode holder 5 made of an insulation material in a condition where the electrode surfaces are exposed as shown in FIG. 2. Three electrodes 4 are disposed in a raw, and the electrodes 4a and 4b at both sides constitute AC current supply electrodes connected to a power source, and the electrode 4c at the center position constitutes an detection electrode functioning as a sensor for detecting electric conductivity.

Electrode holder 5 is fixed at a predetermined position of a substrate 6. In the substrate 6, inlet 7 for introducing a fluid to be measured (for example, an aqueous solution), outlet 8 for discharging the fluid, and flow holes 9 and 10 for measuring electric conductivity are provided. In the electrode holder 5, flow hole 11 and 12 are provided, and the flow hole 11 is disposed to communicate with the flow hole 9 of the substrate, and the flow hole 12 is disposed to communicate with flow hole 10 of the substrate, respectively. A fluid to be measured introduced from inlet 7 is sent into a space 14 for storing a substance to be measured, which is defined on the side of the electrode surfaces of the respective electrodes 4, through an inside path 13 of the substrate 6, the flow hole 9, and the flow hole 11 of electrode holder 5. The space 14 for storing a substance to be measured forms a flow path for measuring electric conductivity of the fluid to be measured. The fluid from the space 14 for storing a substance to be measured is discharged from outlet 8 through the flow hole 12 of electrode holder 5, the flow hole 10 of the substrate 6, and an inside path 15.

In the substrate 6, through holes 16a, 16b, 16c are opened at positions corresponding to the respective electrodes 4a, 4b, 4c, and necessary electric wires are pulled out of the through holes 16a, 16b, 16c.

The space 14 for storing a substance to be measured, in this embodiment, is defined by a sheet-like packing 17, and a transparent glass plate 18 provided as a light transmitting material which is disposed to confront electrode holder 5 with a gap via packing 17. It is preferred that a titanium oxide coating layer is provided to such an extent that the light transmitting property is not impaired, also to the surface of glass plate 18 on its side facing the space 14 for storing a substance to be measured. The electric conductivity of the fluid, flowing in space 14 for storing a substance to be measured, is measured.

Electrode holder 5, packing 17 and glass plate 18 are fixed to a cover body 20 on one surface side of substrate 6 by bolts 19. A window 21 for transmitting light is opened on cover body 20. Through this window 21, light from light irradiating means 22 which is disposed outside is irradiated. Light irradiated is shed on titanium oxide layers 3 that form the electrode surfaces of the respective electrodes 4a, 4b, 4c through glass plate 18 from the window 21. Light having a wavelength that brings about a photocatalytic activity of titanium oxide layers 3 is selected as the light to be irradiated. For example, an ultraviolet ray with a specified wavelength (for example, a wavelength falling within a range of 300 to 400 nm) can be employed, and as light irradiating means 22, for example, a black light that irradiates ultraviolet rays can be used.

In the apparatus 31 for measuring electric conductivity according to the first embodiment of the present invention indicated in FIG. 1 as a basic formation of the present invention, an electric conductivity detection electrode 34 is electrically shielded against a grounded point which would exist at any position of the extending portion of measurement tube 32 by two AC current supply electrodes 35, 36, which are disposed on both sides of the electric conductivity detection electrode 34, and to which AC current of a same phase is supplied. Namely, since a constant voltage AC current with a same potential is applied to the two AC current supply electrodes 35, 36, and the potential differences between the electric conductivity detection electrode 34 and the AC current supply electrode 35, 36 are always maintained at predetermined constant values, substantially no electric resistance exists between the electric conductivity detection electrode 34 and an outside grounded point. Therefore, a resistance between an electric conductivity detection electrode and an outside grounded point, and an affection to an output electric current from the electric conductivity detection electrode originating from a variation of the resistance, in a conventional apparatus as explained using FIG. 8, disappear substantially completely. In other words, leaked electric current from the electric conductivity detection electrode 34 to the outside grounded point does not exist at all. As a result, the output electric current from the electric conductivity detection electrode 34 is always extracted at a condition with no disturbance, and scattering and variation of the measured data due to the disturbance are prevented, thereby ensuring a stable and high-accuracy measurement of electric conductivity at all times.

Further, if the portion for measuring electric conductivity of this apparatus 31 for measuring electric conductivity is constituted as the electric conductivity meter 1 shown in FIG. 2, by irradiating light from light irradiating means 22, titanium oxide layers 3 provided on the surfaces of the respective electrodes 4a, 4b, 4c exhibit a photocatalytic activity. Therefore, even when organic substances are contained in a fluid to be measured flowing in the space 14 for storing a substance to be measured, because the organic substances are decomposed by the photocatalytic activity, even if ion exchange takes place on the electrode surfaces during the measurement of electric conductivity, the nonconductive organic substances are prevented from adhering or being adsorbed onto the electrode surfaces. As a result, a periodical cleaning of the electric surfaces is not required any longer, and electric conductivity can be measured stably and accurately at all times without any cleaning. Further, reproducibility of such a high-accuracy measurement can also be ensured.

Further, if a titanium oxide coating layer is provided on the surface of glass plate 18 on its side facing the space 14 for storing a substance to be measured, the adhesion or adsorption of organic substances to this surface side is also prevented, and accumulation of the organic substances in the space 14 for storing a substance to be measured is prevented, thereby maintaining the high-accuracy measurement.

Figure 4:
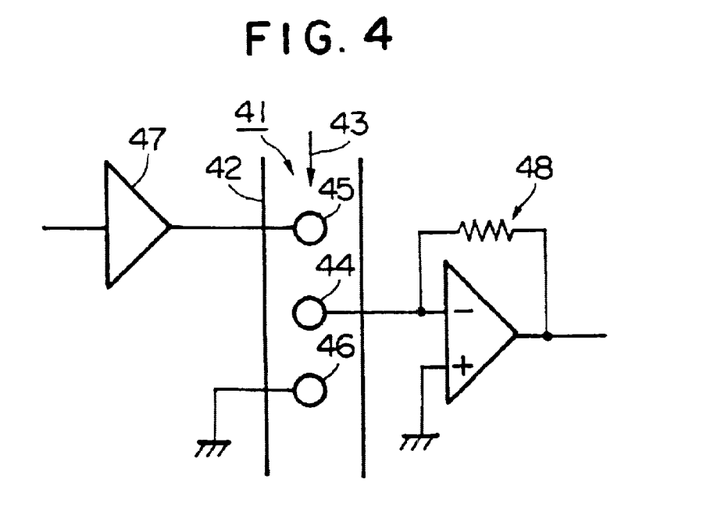
FIG. 4 is a schematic block diagram of an apparatus for measuring electric conductivity according to a second embodiment of the present invention.

FIG. 4 shows an apparatus for measuring electric conductivity according to a second embodiment of the present invention. In this apparatus 41 for measuring electric conductivity, three electrodes 44, 45, 46 brought into contact with a fluid 43 to be measured are provided against the fluid 43 to be measured as a substance to be measured, that is sent into an insulated measurement tube 42, or that is stored in the measurement tube 42. The three electrodes comprise a detection electrode 44 for detecting electric conductivity, an AC current supply electrode 44 disposed on one side of the electric conductivity detection electrode 44 at a distance, and a grounded electrode 46 disposed on the other side of the electric conductivity detection electrode 44 at a distance. A predetermined AC current is supplied at a constant voltage to the AC current supply electrode 45 through an amplifier 47. The electric conductivity detection electrode 44 is connected to an electric current amplifier 48, and an amplified electric current is extracted as a value corresponding to the electric conductivity of the fluid 43 to be measured through the electric current amplifier 48. This apparatus 41 for measuring electric conductivity can also be constituted as an electric conductivity meter, for example, similar to that shown in FIG. 2.

In the apparatus 41 for measuring electric conductivity according to the above-described second embodiment, an AC current with a constant voltage is supplied to only the AC current supply electrode 45, the grounded electrode 46 is forcibly made zero in potential by grounding, and these electrodes 45, 46 are disposed on both sides of the electric conductivity detection electrode 44. Therefore, the portion between the electrodes 45, 46 is in a condition of so-called resistive division in electric circuit formation, divided by electric conductivity detection electrode 44. In the circuit between these electrodes 45, 46, a predetermined AC current with a constant voltage is applied to the electrode 45, and the potential of the electrode 46 is always made forcibly to be zero due to grounding, and this condition is always stable. Namely, even if any extending portion of the measurement tube 42 is grounded, there is no room which allows a resistance to enter between the grounded point and the electric conductivity detection electrode 44, and whereby, the electric current extracted from the detection electrode 44 does not shift and does not vary. Therefore, the output electric current from the electric conductivity detection electrode 44 can be extracted at a condition with no disturbance at all times, and scattering and variation originating from the disturbance can be prevented, and a stable and high-accuracy measurement of electric conductivity can be ensured at all times.

Further, if the portion for measuring electric conductivity of this apparatus 41 for measuring electric conductivity is constituted as electric conductivity meter 1 shown in FIG. 2, operation and advantages similar to those in the aforementioned first embodiment can be obtained, and more stable measurement, capable of preventing adhesion and adsorption of organic substances, becomes possible.

Figure 5:
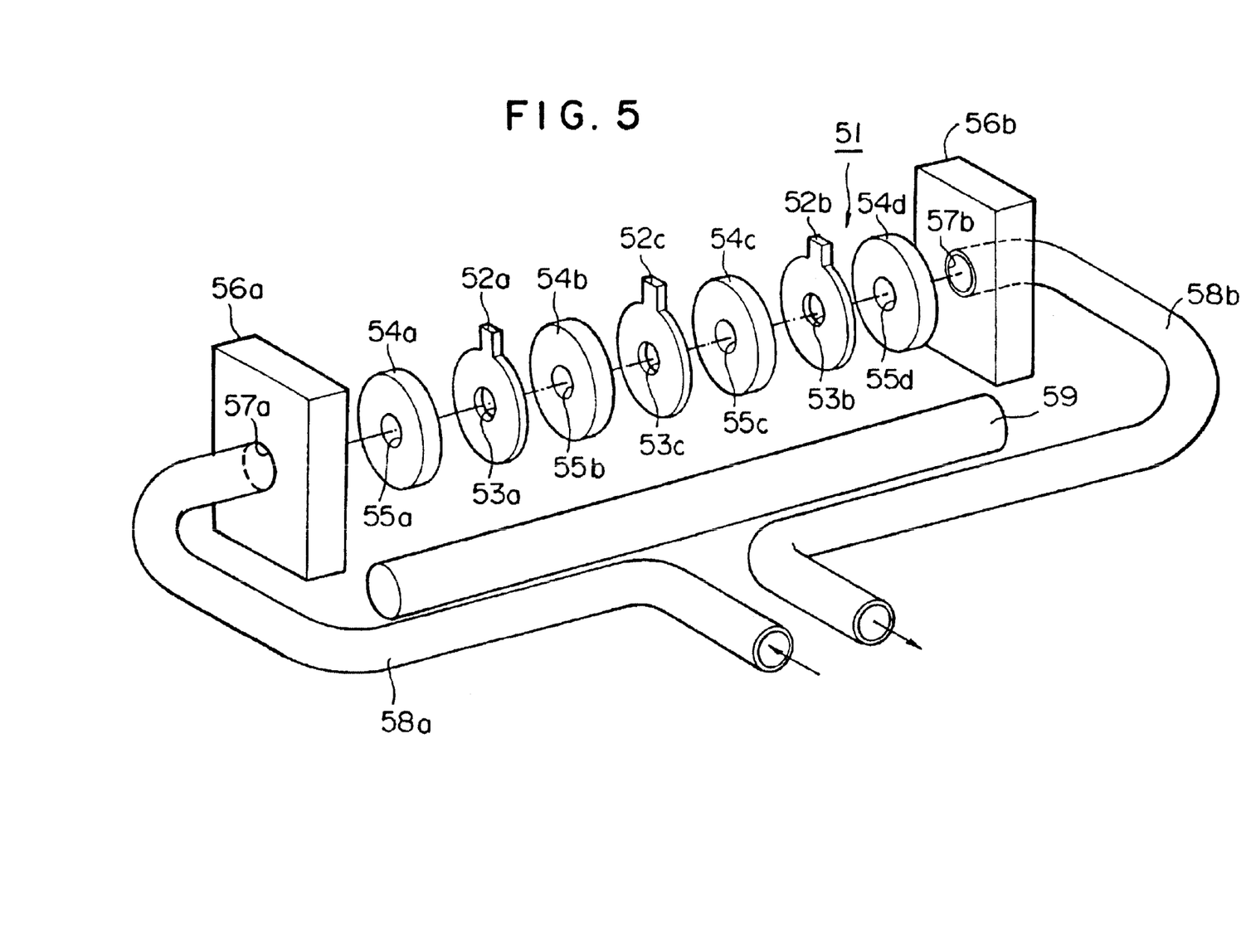
FIG. 5 is an exploded perspective view of another example wherein a portion for measuring electric conductivity of an apparatus for measuring electric conductivity according to the present invention is constructed as an electric conductivity meter.

Further, the portion for measuring electric conductivity of an apparatus for measuring electric conductivity according to the present invention also can be constituted, for example, as an electric conductivity meter 51 shown in FIG. 5, in order to make it smaller and thinner. In the electric conductivity meter 51 shown in FIG. 5, three electrodes 52a, 52b, 52c are provided, and for example, the electrode 52a, 52b on both sides are constituted as power supplying electrodes connected to a power source, and the electrode 52c disposed between them is constituted as a detection electrode functioning as a sensor for detecting an electric conductivity. Through holes 53a, 53b, 53c are opened at the central portions of the respective electrodes 52a, 52b, 52c, and titanium oxide layers are provided on the inner surfaces of the respective holes 53a, 53b, 53c. Spacers 54a, 54b, 54c, 54d made of a light transmitting insulation material (for example, 4-fluoride ethylene) are disposed on both sides of the respective electrodes 52a, 52b, 52c, and the respective electrodes and spacers are stacked alternately. Through holes 55a, 55b, 55c, 55d are opened also in the central portions of spacers 54a, 54b, 54c, 54d, respectively. Support materials 56a, 56b are disposed outside of spacers 54a, 54d positioned at both sides, and a stacked body comprising the electrodes 52a, 52b, 52c and the spacers 54a, 54b, 54c, 54d are sandwiched from both sides by the support materials. Through holes 57a, 57b are opened also in the central portions of the respective support materials 56a, 56b, and into the holes 57a, 57b, one end of a tube 58a for introducing a fluid to be measured, and one end of a tube 58b for discharging the fluid are inserted and fixed, respectively.

A flow path of a fluid to be measured is formed by holes 55a, 53a, 55b, 53c, 55c, 53b, 55d connected by stacking the electrodes 52a, 52b, 52c and the spacers 54a, 54b, 54c, 54d. A fluid to be measured introduced through tube 58a is discharged through tube 58b, after flowing inside of this flow path. These tubes 58a, 58b are composed of a light transmitting material (for example, 4-fluoride ethylene), and an ultraviolet ray with a predetermined wavelength is irradiated from black light 59 provided as means for irradiating light. As the ultraviolet ray irradiated repeats diffusion and reflection in tubes 58a, 58b while transmitting the tubes, the ultraviolet ray is guided along the tubes 58a, 58b, and guided to the inner surfaces formed by titanium oxide layers in the respective electrodes 52a, 52b, 52c from the portions of holes 57a, 57b at both sides. Further, as the respective spacers 54a, 54b, 54c, 54d are also composed of a light transmitting material, the ultraviolet ray from black light 59 is irradiated to the inner surfaces of electrodes 52a, 52b, 52c after transmitting each spacer while utilizing diffusion and reflection. Especially, by forming each electrode and spacer to be relatively thin (for example, the thickness of each electrode is about 0.2 mm, and the thickness of each spacer is about 1 mm), because the flow path formed by the respective electrodes and spacers becomes relatively short, even if a particular light transmitting material such as an optical fiber is not used, a sufficient amount of light for measurement is irradiated onto predetermined electrode surfaces by the light guiding along light transmitting tubes 58a, 58b as described above, and by the light guiding through light transmitting spacers 54a, 54b, 54c, 54d. Therefore, in this embodiment, a simpler and smaller unit can be constructed.

EXAMPLES

The following examinations were carried out with respect to the apparatuses for measuring electric conductivity shown in FIG. 1 and FIG. 4, and performance thereof was determined.

Example 1

Figure 6:
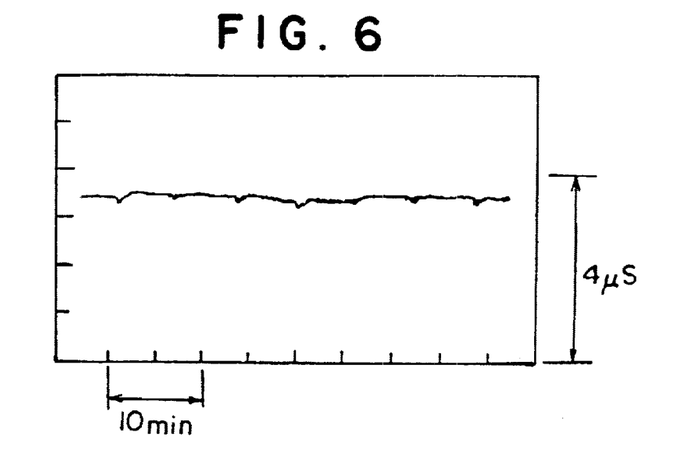
FIG. 6 is a chart indicating a measurement result of Example 1.

An apparatus for measuring electric conductivity having three electrodes (all of three electrodes were not grounded) shown in FIG. 1 was constructed, a sodium chloride solution having a conductivity of 240 $\mu$S was used as a solution to be measured, and the electric conductivity of the solution was measured. The temperature of the measuring cell was controlled at 45° C. relative to the room temperature of 25° C. at the time of measurement. The flow rate of the solution into the measuring cell was set at 1 ml/min. The result is shown in FIG. 6.

Example 2

Figure 7:
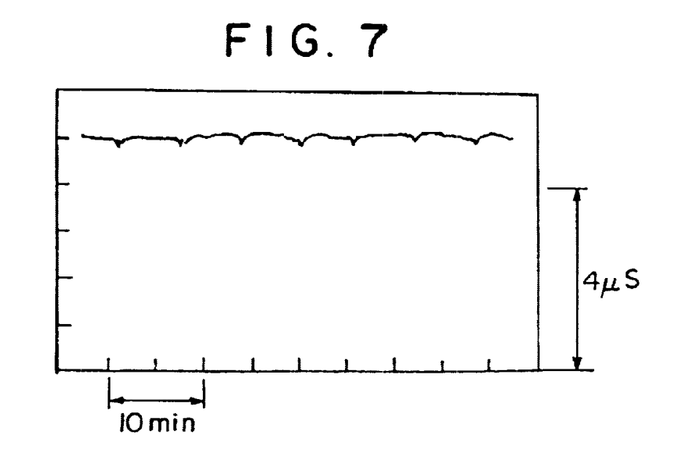
FIG. 7 is a chart indicating a measurement result of Example 2.

An apparatus for measuring electric conductivity having three electrodes (one electrode of one side was grounded) shown in FIG. 4 was constructed, a sodium chloride solution having a conductivity of 240 $\mu$S was used as a solution to be measured, and the electric conductivity of the solution was measured. The temperature of the measuring cell was controlled at 45° C. relative to the room temperature of 25° C. at the time of measurement. The flow rate of the solution into the measuring cell was set at 1 ml/min. The result is shown in FIG. 7.

Comparative Example 1

Figure 8:
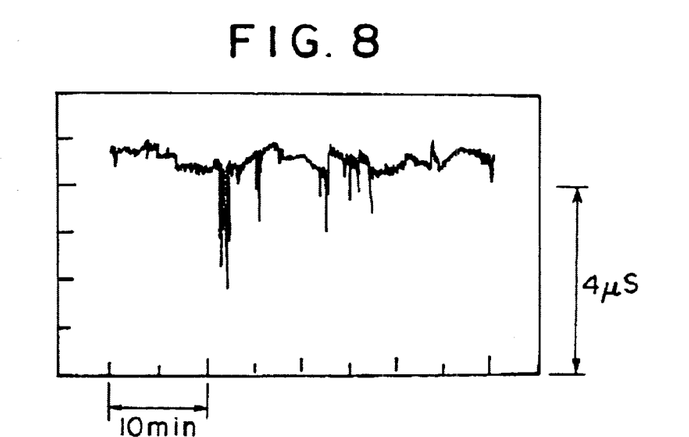
FIG. 8 is a chart indicating a measurement result of Comparative Example 1.

An conventional apparatus for measuring electric conductivity having two electrodes shown in FIG. 9 was constructed, a sodium chloride solution having a conductivity of 240 $\mu$S was used as a solution to be measured, and the electric conductivity of the solution was measured. The temperature of the measuring cell was controlled at 45° C. relative to the room temperature of 25° C. at the time of measurement. The flow rate of the solution into the measuring cell was set at 1 ml/min. The result is shown in FIG. 8.

In the above-described Example 1, as shown in FIG. 6, variations due to noises and the like were less, and a stable result could be obtained with a high accuracy. In Example 2, as shown in FIG. 7, a shift in potential based on the offset caused by grounding one electrode was observed, as compared with Example 1, but variations due to noises and the like were less, and a stable result could be obtained with a high accuracy, similarly to the result of Example 1. In Comparative Example 1, as shown in FIG. 8, a noise originating from a disturbance was picked up as compared with Example 1 and Example 2, the measured data greatly varied, and a stable result with a high accuracy could not be obtained. Since the disturbance in Comparative Example 1 was almost in correspondence with the operation of connection/disconnection of the air conditioner and the switching operation of the solenoid of the electromagnetic valve located nearby, the disturbance is considered to be noises originating from these operations.

INDUSTRIAL APPLICATION OF THE INVENTION

In the apparatus for measuring electric conductivity according to the present invention, electric conductivity can be measured stably and accurately in a condition with no variation, for a substance to be measured such as an aqueous solution, a gaseous substance or a slurry-like substance, especially for an aqueous solution. Especially, ion concentration in an aqueous solution can be measured with a high accuracy by this measurement of electric conductivity.

What is claimed is:

1. An apparatus for measuring electric conductivity comprising three electrodes brought into contact with a substance to be measured, said three electrodes including a detection electrode for detecting electric conductivity of the substance to be measured, and two AC current supply electrodes disposed on both sides of said electric conductivity detection electrode at respective distances, an AC current of the same phase being applied to said two AC current supply electrodes, and said apparatus having a space for storing a substance to be measured which is defined between respective electrode surfaces of said three electrodes, and light irradiating means for irradiating light onto the respective electrode surfaces, wherein said light irradiating means comprises a light guiding material which guides light from a light source.

2. An apparatus for measuring electric conductivity comprising three electrodes brought into contact with a substance to be measured, said three electrodes including a detection electrode for detecting electric conductivity of the substance to be measured, and two AC current supply electrodes disposed on both sides of said electric conductivity detection electrode at respective distances, an AC current of the same phase being applied to said two AC current supply electrodes, and said apparatus having a space for storing a substance to be measured which is defined between respective electrode surfaces of said three electrodes, and light irradiating means for irradiating light onto the respective electrode surfaces, wherein said space for storing a substance to be measured is defined by a light transmitting material, and light from said light irradiating means is irradiated onto said electrode surfaces through said light transmitting material.

3. The apparatus for measuring electric conductivity according to claim 2, wherein a titanium oxide coating layer capable of transmitting light is provided on a surface of said light transmitting material of its side facing said space for storing a substance to be measured.

4. An apparatus for measuring electric conductivity comprising three electrodes brought into contact with a substance to be measured, said three electrodes including a detection electrode for detecting electric conductivity of the substance to be measured, an AC current supply electrode disposed on one side of said electric conductivity detection electrode at a distance, and a grounded electrode disposed on the other side of said detection electrode at a distance, and said apparatus having a space for storing a substance to be measured which is defined between respective electrode surfaces of said three electrodes, and light irradiating means for irradiating light onto the respective electrode surfaces, wherein said light irradiating means comprises a light guiding material which guides light from a light source.

5. An apparatus for measuring electric conductivity comprising three electrodes brought into contact with a substance to be measured, said three electrodes including a detection electrode for detecting electric conductivity of the substance to be measured, an AC current supply electrode disposed on one side of said electric conductivity detection electrode at a distance, and a grounded electrode disposed on the other side of said detection electrode at a distance, and said apparatus having a space for storing a substance to be measured which is defined between respective electrode surfaces of said three electrodes, and light irradiating means for irradiating light onto the respective electrode surfaces, wherein said space for storing a substance to be measured is defined by a light transmitting material, and light from said light irradiating means is irradiated onto said electrode surfaces through said light transmitting material.

6. The apparatus for measuring electric conductivity according to claim 5, wherein a titanium oxide coating layer capable of transmitting light is provided on a surface of said light transmitting material of its side facing said space for storing a substance to be measured.

* * * * *